United States Patent [19]

Coveney et al.

[11] Patent Number: 6,009,419

[45] Date of Patent: Dec. 28, 1999

[54] METHOD FOR PREDICTING CEMENT PROPERTIES

[75] Inventors: Peter Vivian Coveney, Epping; Philip Fletcher, Aberdeen, both of United Kingdom

[73] Assignee: Schlumberger Technology Corporatin, Sugar Land, Tex.

[21] Appl. No.: 08/897,400

[22] Filed: Jul. 21, 1997

Related U.S. Application Data

[63] Continuation of application No. 08/244,324, filed as application No. PCT/GB92/02216, Nov. 30, 1992, abandoned.

[30] Foreign Application Priority Data

Nov. 29, 1991 [GB] United Kingdom .................. 9125426

[51] Int. Cl.⁶ ..................................................... G06F 15/18
[52] U.S. Cl. ................................ 706/16; 706/15; 706/21; 73/64.41; 73/64.43
[58] Field of Search .................................. 395/20–25, 27; 382/155–161; 367/87, 35; 324/300; 706/14–16, 21, 25, 26, 27; 73/64.41, 64.43

[56] References Cited

U.S. PATENT DOCUMENTS

| | | | |
|---|---|---|---|
| 3,615,223 | 10/1971 | Burroughs et al. | 356/409 |
| 3,747,702 | 7/1973 | Beil | 367/87 |
| 4,259,868 | 4/1981 | Rao et al. | 73/597 |
| 4,382,290 | 5/1983 | Havira | 367/35 |
| 4,648,264 | 3/1987 | Freese et al. | 73/64.41 |
| 4,979,124 | 12/1990 | Sachse et al. | 702/38 |
| 5,672,968 | 9/1997 | Miller et al. | 324/300 |

FOREIGN PATENT DOCUMENTS

| | | | |
|---|---|---|---|
| 1038698A | 1/1990 | China . | |
| 2 111 193 | 6/1983 | United Kingdom | G01N 21/47 |
| 2 221 042 | 1/1990 | United Kingdom | G01F 1/94 |

OTHER PUBLICATIONS

Akalp et al, "Supervisory Fuzzy control of a rotary cement kiln," 1994 IEEE Mediterranean Electrotechnical Conference, pp. 754–757 vol. 2, Apr.

Constantinescu et al, "Towards the fault–tolerant control of a cement plant," Second international conference on Factory 2001–integrating information and material flow, pp. 168–172, Jul. 1990.

Clarke, "Application of generalized predictive control to industrial processes," IEEE Control systems magazine, vol. 8, iss. 2, pp. 49–55, Apr. 1988.

(List continued on next page.)

*Primary Examiner*—Tariq R. Hafiz
*Assistant Examiner*—Jason W. Rhodes
*Attorney, Agent, or Firm*—Douglas Y'Barbo

[57] ABSTRACT

A method of predicting a desired property, such as thickening time, of a cement slurry comprising measuring or determining other properties of a slurry composition and obtaining a predicted value of the desired property by applying values representative of the other properties to a model formed by determining the other properties for a series of cement compositions and correlating these with measured values of the desired property. In one embodiment the method comprises measuring and determining the other properties and inputting values corresponding to these properties to a neural network device configured to output a value representative of the desired property, the neural network device being a) configured to utilize each of said values as input values, b) provided with at least one hidden layer of at least one node, and c) trained with a dataset comprising series of values of said properties and a value corresponding to the desired property when measured for a slurry having the measured properties.

16 Claims, 3 Drawing Sheets

INPUT LAYER  HIDDEN LAYER  OUTPUT LAYER

OTHER PUBLICATIONS

Boscolo et al, "Fuzzy sensor data fusion for quality monitoring in concrete mixing plant," Conference Record IMTC/93 pp. 671–675, May 1993.

Bensted, J. "Chemical Aspects of Normal Setting of Portland Cement," Engineering Foundation, No. 82–15, pp. 69–86, Jul. 1982.

Rebagay, T.V., and Dodd, D.A., Quantitative Diffuse Reflectance Infrared Fourier Transform Spectrometric Studies of Cementitious Blends, WHC–SA–0–0493–FP, Westinghouse Hanford Company, p. 1, Jul. 1989.

Hertz et al., Introduction to the Theory of Neural Computation, Addison–Wesley, p. 142, 1991.

J. Bensted, Oilwell Cements—Characterization by Infrared Spectroscopy, II Cemento, pp. 35–46, 1987.

Soukhanov et al., Webster's II New Riverside University Dictionary, The Riverside Pub. Co., p. 314, 1994.

Lee P. Hunt, "Prediction of Thickening Time of Well Cements from Blaine Air Permeability," *Cement and Con–Crete Research*, vol. 16, pp. 190–198 (1986).

Thierry Simien et al., "A Cement Slurry Design System," pp. 39–45, from Fourth Annual Conference on A1 in Petroleum Exploration and Production, Texas A&M University (1991).

R. H. Bogue, "Calculation of the Compounds in Portland Cement," *Industrial and Engineering Chemistry, Analytical Edition*, vol. 1, No. 4, pp. 192–197 (1929).

INPUT LAYER    HIDDEN LAYER    OUTPUT LAYER

METHOD FOR PREDICTING CEMENT PROPERTIES

This application is a continuation of application Ser. No. 08/244,324, filed on May 25, 1994, now abandoned, which is a 371 of PCT/GB92/02216 filed Nov. 30, 1992.

The present invention relates to a method for predicting properties of cement. In particular, the method provides a method of predicting the thickening time of a cement slurry although it is by no means restricted to this use.

In oilwell drilling, cement is used to secure a lining or casing inside a drilled hole. The casing is usually a steel tube and cement slurry is pumped between the casing and the borehole wall and allowed to set, so securing the casing in place. Casing is cemented into a borehole for various reasons. The casing prevents any enlargening of the hole by contact with the drill string or erosion by drilling mud and cuttings. This is particularly important where the borehole encounters soft underground formations. The cement also provides a seal between underground formations so that, for example, water at one level is not contaminated by oil flowing from another level via the borehole. Cement also seals the drilled wall of the borehole which can prevent gas entering the well while it is being drilled which can cause blow-out.

In a typical cementing operation, casing is run into the borehole and cement is pumped from the surface through the casing such that it fills the annulus between the outer surface of the casing and the borehole wall from the bottom up. During this operation it is necessary for the cement to flow relatively easily so that it can be pumped and can fill the entire annulus. Once the cement is in place, it is desirable that it should set in a relatively short time in order that drilling can recommence. The time after mixing a cement slurry at which pumping is no longer possible because the cement has started to set is known as the thickening time and the composition of the slurry is selected according to the required thickening time. A knowledge-based slurry design system has been proposed by Dowell Schlumberger of Saint Etienne, France (see paper from Fourth Annual Conference on Artificial Intelligence in Petroleum Exploration and Production, Texas A&M University 1991) which relies on a large cement slurry database which can be consulted for proposals of slurries according to the conditions chosen. Before a slurry is pumped into a well, it is necessary to test the thickening time of a sample of the slurry. Thickening time measurements are made in a pressurised consistometer which conforms to the specification defined in API Spec. 10. The measurement is performed by first mixing a cement slurry, in accordance with a defined procedure and specified solid to water ratio, prior to placing a required quantity of the slurry in a suitably calibrated consistometer. The subsequent consistometry measurement involves raising the temperature and pressure of the cement to specified values at specified rates while a consistency measurement is being made. After reaching the specified conditions, the temperature and pressure are stabilised and the consistency of the cement is measured continuously. The time at which the cement reaches a specified consistency is the thickening time. Thickening times can be measured in accordance with one of 20 different schedules. Each schedule has a specified heating rate leading to a specified final temperature and pressure.

Since the standard API measurement attempts to simulate, to some degree, the conditions encountered in a well, the time taken to test each slurry is considered to be close to the actual thickening time of the cement which can often be in the order of 3–6 hours. This, together with the nature of the equipment used, makes thickening time measurement expensive in terms of both cost and time.

It has been previously proposed to predict the thickening time of a cement by measuring one or more properties of the neat cement powder. This technique is based on regression analysis of the measured properties and observed thickening time (see *Cement and Concrete Research.* Vol 16. pp 190–198, 1986 Pergamon Press Ltd, *Prediction of thickening time of well cements from Blaine air permeability,* L P Hunt). In this article, it is proposed to predict thickening time of class G and H cements from measurement of Blaine fineness of the neat cement powder using a linear regression analysis technique. While other properties are measured and do improve the prediction, it is proposed that only the fineness measurement is worth measuring. It is not known whether this method has even been used successfully and is considered of doubtful value since only properties of neat cement are measured and other factors known to affect thickening time of a slurry are ignored, eg the presence of a retarder or accelerator.

GB 2111 193 A describes a method for assessing the quality of cement clinker comprising illuminating the clinker with an infra-red source and maintaining the reflected light The reflectance colour is affected by the free CaO content which determines the quality of the clinker.

It is an object of the present invention to provide a method which can usefully predict the time developing properties of a cement slurry such as thickening time or which can usefully replace experimental techniques for the determination of such a property.

In its broadest aspect, the present invention provides a method of predicting a desired property, such as thickening time, of a cement slurry comprising measuring or determining other properties of a slurry composition and obtaining a predicted value of the desired property by applying values representative of the other properties to a model formed by determining the other properties for a series of cement compositions and correlating these with measured values of the desired property.

In one embodiment the method comprises measuring and determining the other properties and inputting values corresponding to said properties to a neural network device configured to output a value representative of the desired property, the neural network device being a) configured to utilise each of said values as input values, b) provided with at least one hidden layer of at least one node, and c) trained with a dataset comprising series of values of said properties and a value corresponding to the desired property when measured for a slurry having the measured properties.

In another embodiment, the invention comprises obtaining the infrared spectrum of the cement or cement slurry and correlating this information with a time developing property such as thickening time to provide the appropriate model which is consulted when an unknown cement is tested. The infrared spectra can be analysed by the neural network arrangement specified above or any suitable multivariate statistical method.

The present invention will now be described by way of example, with reference to the accompanying drawings, in which.

The thickening time of a cement is dependent on a number of properties including the mineral composition of neat cement, the amounts and relative proportions of additives and the thickening time schedule. The complex inter-relationships are difficult to define and have so far defied comprehensive mathematical description. One embodiment of the present invention proposes using computer-based artificial neural networks as the framework for predicting thickening times from measurable properties of cement.

The basic unit of an artificial neural network is the neuron or node. In computational terms this comprises a processing element which combines a set of numerical inputs to produce a single numerical output. The neuron generates an output signal in response to the input signals it receives, the strength of which is usually the sum of all the input signals transformed by a mathematical expression called a "transfer function".

Figure 1:
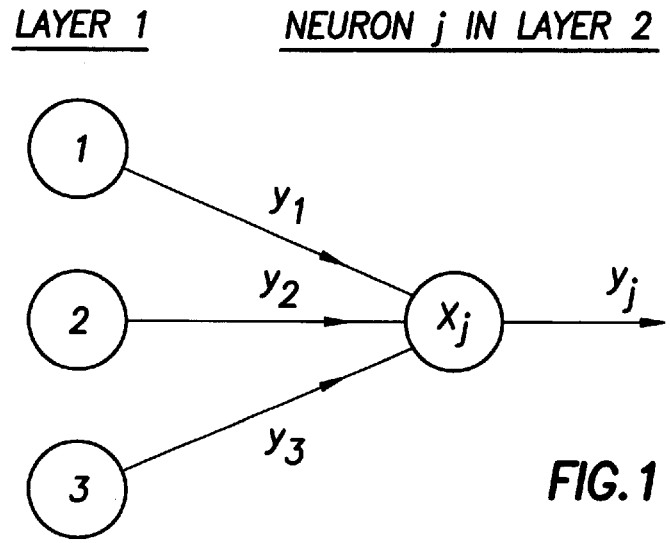
FIG. 1 shows a schematic view of a single neuron in an artificial neural network.

FIG. 1 shows a schematic of a simple neuron system. Each neuron in layer 1 is ascribed a number $y_i$ which is to be thought of as its output value. The ith neuron makes a contribution to the input for neuron j which is equal to the value of $y_i$ multiplied by a weighting factor $W_{ij}$. The summation of the individual contributions from all neurons in the ith layer is called the activation of neuron j. Algebraically, the activation $X_j$ is calculated from:

$$X_j = \sum_i y_{ij} - \theta_j, \qquad (1)$$

where $\theta_j$, is an empirical coefficient called the bias of neuron j. The weighted sum is the most common activation function but others are sometimes used. Occasionally input signals are multiplied rather than summed. Once $X_j$ is known, the output value of neuron j, $y_j$, is calculated from the transfer function:

$$y_i = f(X_j). \qquad (2)$$

The most common transfer function is a sigmoid:

$$f(X_j) = \frac{1}{1 + e^{-X_j}}. \qquad (3)$$

However, other transfer functions may also be used such as linear or hyperbolic tangent.

Figure 2:
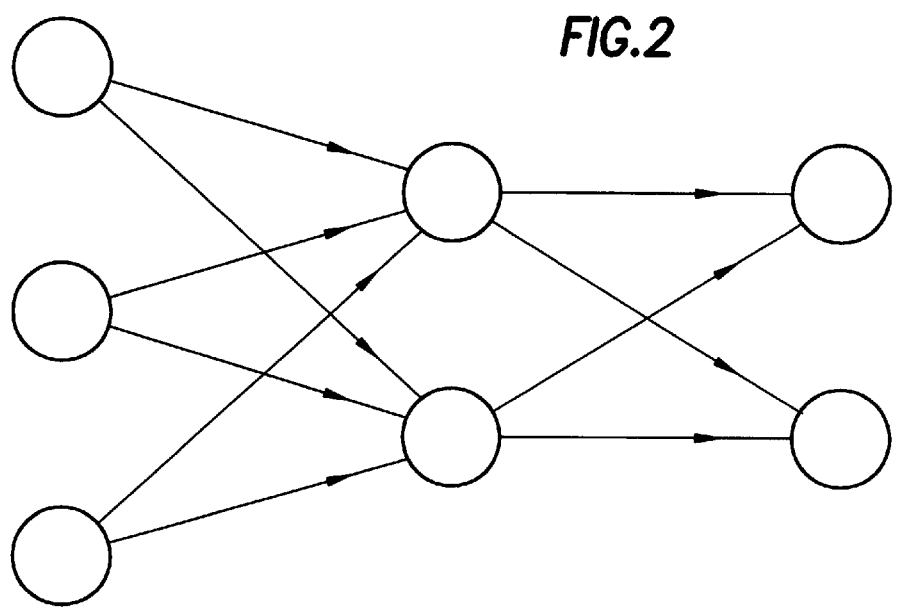
FIG. 2 shows a schematic view of a simple artificial neural network.

Any number of neurons may be arranged to construct an artificial neural network. Networks are composed of layers of neurons where the outputs from neurons in one layer constitute the inputs to neurons in the next layers. Layers between the input and output layers are called hidden layers. The structure forms a complex interrelated network which accepts numerical signals from input variables and transmits these signals through the network such that the outputs are a modified representation of the combined inputs as in FIG. 2. The general objective is to select a network architecture and a set of weights obtaining by training such that, for given input data, the outputs from the final layer match the values of selected dependent variables or target values with an acceptable tolerance.

Different network architectures are distinguished by the number of layers of nodes, the number of nodes in each layer and the extent to which the nodes are connected. Common network architectures have each node connected to every node in the preceding layer but unconnected to nodes in the same layer. The most useful and general neural network is called the multilayer perceptron (MLP). This type of network has one or more hidden layers for which the connectivity between the nodes can be varied according to the problem in question. In fact, it can be shown that any non-linear mapping needs no more than two hidden layers but generally it is preferable to restrict this number to one since additional layers greatly increase training times. The topology, the connection weights and the activation levels are together called the internal representation of the neural network.

Once a network architecture has been selected, the computational issues are concerned with determining values of the connection weights which minimise the difference between the network outputs and the target values. The technique for optimising the weights in a MLP is an iterative technique called back propagation (Rumelhart D E and McClelland J L, eds. "Parallel Distribution Processing: Explorations in the Microstructure of Cognition", 1986, Volume 1, *Foundations,* MIT Press). The technique, which is a variation on the method of steepest descent (Press W H, Flannery B P, Teukolsky S A, and W T Vetterling, "Numerical Recipes: The Art of Scientific Computing", 1986, Chapter 10, Cambridge University Press), minimizes the difference between the predicted output and the true output. The procedure for optimising the fitting parameters is called training. The prediction of the target variables for an independent dataset, on which the network has not been trained, is called generalisation.

There are two major factors which need to be considered in order to ensure that a neural network can generalise. These are (a) the nature and quality of data and (b) the architecture of the neural network. As a rule, the number of required examples for training is about ten times the number of input plus output variables, although the number may vary from problem to problem. At the present time, there are no known rules which can be invoked to determine the optimum network topology for any given problem: the selection of an appropriate architecture is to a large extent a matter of trial and error.

In the present case the data in the input layer and the target values represent determinable or measurable properties of the cement. The input values need not have well established physical relationships with the target variables. For example, in some applications an index number representing a class of cement may be used as an alternative to detailed measurements on the properties of the cement.

In one embodiment of the present invention, an artificial neural network is configured to predict cement thickening times using a primary dataset for training and a commercially available neural network software package such as Neural Works Professional II/Plus (NeuralWare, Inc. Penn Center West, Pittsburg, Pa. 15276, USA).

The primary training dataset includes data on 130 oilfield cements covering classes A, B, C, G and H. The measured data for each cement is shown in Table 2 and includes the following:

(a) The percentage by weight of the cement minerals tricalcium silicate ($C_3S$), dicalcium silicate ($C_2S$), tricalcium aluininate ($C_3A$) and calcium alumino-ferrite (Fer) as predicted by the Bogue calculation (Bogue R H, "Calculation of the compounds in portland cement", Ind. Eng.

Chem. Anal., 1, 192–197, 1929); this data represents four independent input variables in the dataset;

(b) Total percentage by weight of sulphate ($SO_3$);

(c) Blaine surface area in units of $m^2 \, kg^{-1}$ (Blaine);

(d) Percentage by weight of magnesium oxide (MgO), total alkali content (Alk) and free lime (F.Lime) (thee independent input variables);

(e) Percentage loss on ignition (LOI);

(f) Insoluble residue (IR)

(g) Water-to-solid ratio for all cement slurries (W/S);

(h) Weight percent of sodium chloride (NaCl) retarder in some cement blends;

(i) Weight percent of calcium chloride (CaCl) accelerator in some cement blends;

(j) Thickening time schedules defined by well depth (Depth), bottom hole temperature (BHT) and bottom hole pressure (BHP) (3 input variables);

(k) Thickening time to 100 Bearden units (T/100).

In total the input data is characterised by 16 input variables. The data includes no cements known to cause problems in oilfield cementing applications.

Figure 3:
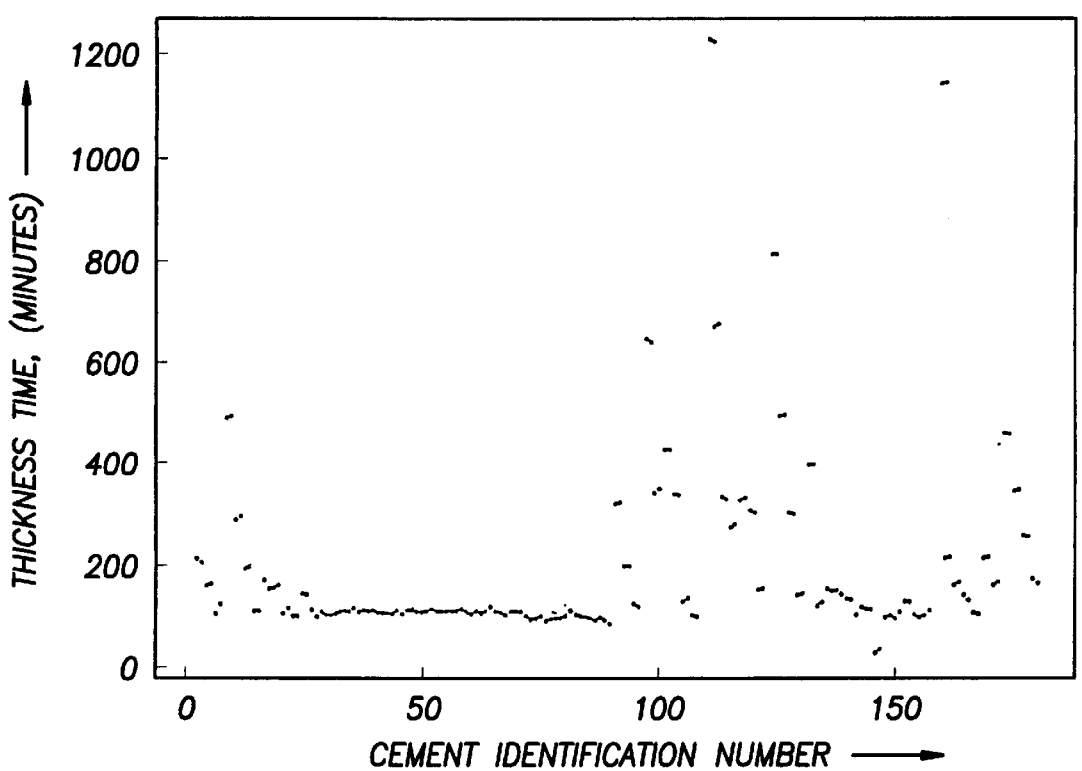
FIG. 3 shows the thickening times for a number of cement compositions in a training set.

FIG. 3 shows the thickening time for 90 cements selected randomly from the primary dataset. The abscissa is the order in which the data was selected. Many of the cements show a thickening time of around 100 minutes although there is a spread of data. The band of measurements in the middle of the plot is for a set of cements which showed little variance in composition, surface area or thickening time. The data at very high thickening times are for a range of cements retarded with sodium chloride. The variation in the mineral compositions and the sulphate contents, for the entire dataset, were within the bounds normally encountered for oil-well cements.

Figure 4:
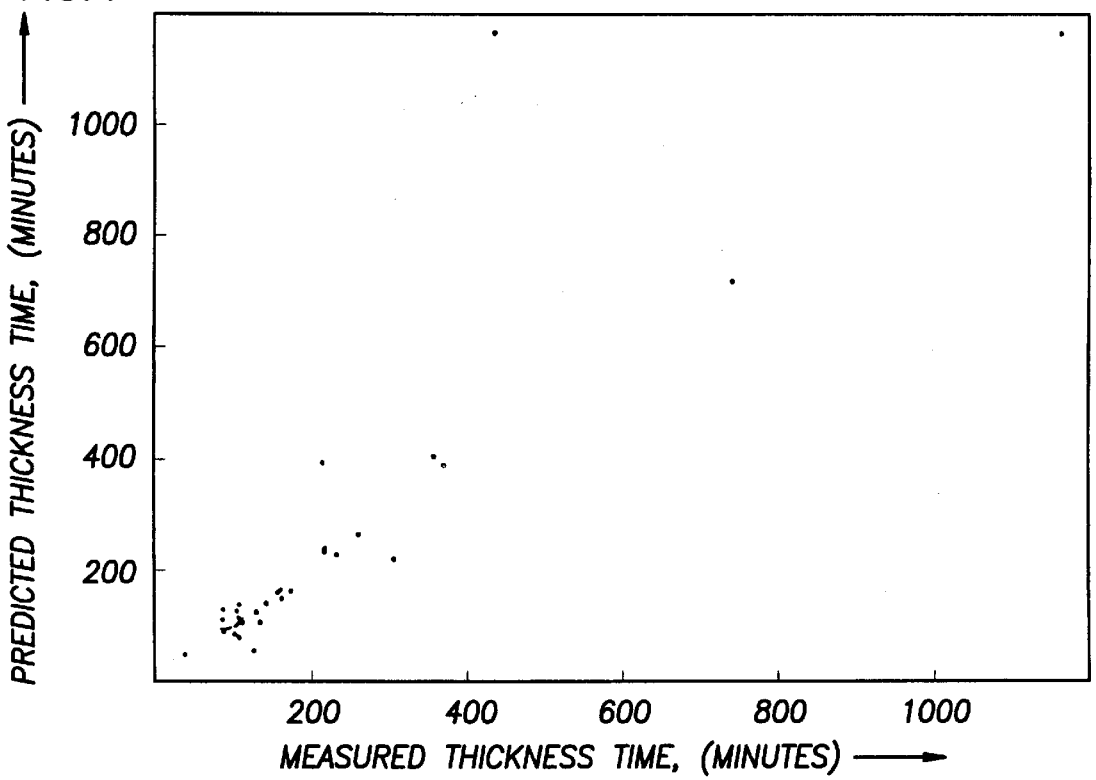
FIG. 4 shows the predicted thickening time plotted against measured thickening times for a variety of compositions.

Initially, a range of networks were trained on this data each having one hidden layer and a single target output which was the thickening time. The number of nodes in the hidden layer was varied between 1 and 12. FIG. 4 shows the predicted and measured thickening times for the calibration data calculated using a network with six nodes in the hidden layer. The mean residual error on the validation is ±16%. Over 80% of the data is predicted with an error of less than 20% and around 50% of the data predicted with an accuracy of better than 5%.

The precision of the network predictions is almost independent of the number of nodes in the hidden layer of the network. This observation is shown in Table 1 which depicts the errors on validation and calibration plus the number of predictions falling below a specified error limit.

In order to deduce the minimum number of input variables necessary to predict thickening times adequately the data set was progressively and systematically reduced and the six node network re-trained after each reduction.

The minimum number of input variables required to predict thickening times of a cement slurry composition with a mean error of less than 17% is 9. These are the 4 basic cement minerals, solid to water/ratio, Blaine surface area, sodium chloride concentration, calcium chloride concentration, and any one from bottom hole pressure, well depth or bottom hole temperature.

Minor improvements could be obtained by including more than the 9 named variables. Reducing the data to less than the number of named variables increased the man error of prediction to 30% or higher.

For neat cements, containing no retarder or accelerator, mean errors in prediction of less than 16% were achieved with seven input variables using the six node network. The 7 input variables are those above excluding sodium chloride or calcium chloride.

The methods herein describe the prediction of a single performance property of oil-well cements from measurable variables including cement composition. It has been proposed that cement composition can be predicted reliably from spectroscopic infrared measurements on the dry cement powder. It is therefore proposed that the composition of the cements may be replaced by specified spectroscopic features of the cement. These features may be digitised interferograms, absorbance measurements at specified frequencies or other parameters designed to compactly represent spectral measurements. The thickening time of cements may be influenced by non-chemical properties of cement particles including particle size distribution, crystallographic defects in cement grains and compositional variations between cement grains. These features and others have subtle effects on the infrared spectra of powders and the spectra therefore contain useful information which may be correlated to thickening times with optimised neural networks along the lines proposed above.

In a second aspect of the invention, the time developing property of the slurry is predicted by analysis of infrared data and, optionally, other data. In a preferred method the Fourier transform infrared (FTIR) spectrum of a sample is obtained. This sample can either be the neat cement powder or a cement slurry analysed a relatively short time after mixing. It has been found that the FTIR spectrum of a cement can be used to predict thickening time by using either a statistical analysis of the data compared to a calibration model or by using an artificial neural network similar to that described above. While predictions can be made from first the FTIR spectrum (typically as 2000 absorbance measurements), it has been found useful to include other data to improve the prediction as will be seen in the following example.

EXAMPLE

In order to test the ability to predict the thickening times of oilfield cements a statistical dataset has been constructed. This contains the following data for each one of 150 class G and class A cements.

FTIR spectrum (2000 absorbance measurements)

Particle size distribution (17 point measurements using a laser diffraction technique)

Blaine surface area ($kg/m^2$)

Loss on ignition (wt %)

Insoluble residue (wt %)

Free lime content (wt %)

Oxide composition (14 oxides measured by inductively coupled optical emission spectrometry, wt %)

Cement minerals (wt % calculated by Bogue, API Bogue and Taylor Bogue methods)

Sulphate minerals (wt % gypsum, bassanite, syngenite, anhydrite)

Calcium hydroxide and calcium carbonate (wt %)

Digitized thickening time profiles

Since there are a large number of data, it is desirable to reduce the amount of data used in the prediction to improve the time required to obtain useful results. The principle involves determining correlations between the selected performance data and the measured properties, in this case thickening time. As an example, a simple linear model may be written in matrix notation as:

$$C = RP. \tag{4}$$

Here, C is matrix of target variables of dimension n×m, where m is the number of target variables for each of the n samples. The matrix R, of dimension p×m, contains values for p measurements on n samples. The matrix P is a regression coefficient matrix of dimensions p×m representing the proportionality between C and R. The matrix P may be determined by one of several common regression techniques.

In multivariate datasets such as the above there may be much redundancy since some measurements may not be truly related to the target variables. Uncorrelated data behaves as noise. this raises problems when using equations such as (4) since noise in the data will be correlated with some proportion of the variance in the target data. The pattern of noise in independent test samples will be different to that in calibration samples. Consequently, the accuracy of subsequent predictions is commonly undermined by a large amount of noisy redundant data. A second problem arises if the values of some measurements are highly correlated in which case the matrix $R^T R$ will have an effective rank less than p and become singular. The simple method of multiple linear regression will then not yield a solution.

The common approach to reducing redundancy in data is Principal Component Analysis (PCA). The method is based on replacing the matrix R with the product of two other matrices T and B. Equation (4) can now be written:

$$C=TBP, \qquad (5)$$

where B has dimensions m×p and B has the dimensions p×p. The decomposition of R into two other matrices is called singular value decomposition, eigenvector projection, factor analysis or principal component analysis depending on the scaling of R. The process of generating the two unique matrices involves an iterative scheme described elsewhere (W Dillon and M Goldstein, 1984, Multivariate Analysis, Chapter 1, Wiley and Sons, New York). The matrix T contains the coordinates of the data in a p dimensional space and the elements of T are called the factor scores or principal components. The matrix B is called the rotation matrix and the elements of B are factor loadings. The columns of T and the rows of B are corthogonal. Theory shows that B is a matrix of eigenvectors of the covariance matrix; it is symmetric and its own transpose.

A linear model to predict composition can be constructed by writing:

$$C=TQ, \qquad (6)$$

where Q=BP. The matrix Q, which has subsumed the rotation matrix and the original coefficient matrix, is itself treated as a set of fitting coefficients which correlate the principal components to the composition matrix. The matrix Q can be determined by the generalised inverse solution $Q=(T^T T)^{-1} T^T C$.

At this stage the technique is identical to multiple linear regression. However, it is possible to truncate the dimensions of B and T to obtain a different result. The key step is to recall that the principal component matrix T is related to the rotation matrix B by R=TB. Since B is symmetric we deduce that:

$$T=RB^T=RB. \qquad (7)$$

That is, given the rotation matrix we may compute the principal component matrix since the columns of the rotation matrix describe the transformation applied to the response matrix to produce the principal component scores. If the number of columns of the rotation matrix (or its transpose) is truncated to k(k<p), yielding a reduced matrix $\bar{B}$ of dimensions p×k, it is possible to compute a truncated principal component matrix $\bar{T}$ of dimensions m×k. We see that the product $\bar{T}\bar{B}^T$ is a response matrix $\bar{R}$ of the same dimensions as the original response matrix (m×p) but composed of less information than the original. Note that in this relationship we must use the transpose of $\bar{B}$ since the truncated matrix is no longer square symmetric. This operation is equivalent to approximating the p dimensional observations pace by projections of the observations onto a smaller k dimensional space. By comparing the original response matrix R with the reduced matrix $\bar{R}$ we can write:

$$C=\bar{T}\bar{B}^T P=\bar{T}\bar{Q}, \qquad (9)$$

where the new matrix $\bar{Q}$, of dimension k×n, contains the regression coefficients which correlate the composition matrix to the truncated principal components matrix. The regression coefficients may be calculated by the generalised inverse method. These coefficients may than be used to predict the concentrations of an independent validation set given the truncated principal component matrix for such data.

In PCA it is important that the data is scaled correctly since the variance contribution of a particular column in the R matrix is dependent on its units of measurements. Normalisation of both target data and input data to common unit variance is often employed although care must be taken not to scale up the variance of variable that are almost constant in order not to disturb the natural relationship amongst variables. Algorithms to normalize data and calculate principal components are part of most standard statistical packages such as S-Plus (S-Plus: User's Manual, Statistical Sciences, Inc., 1991, Washington) and need not be dealt with here.

A feature of above data reduction technique is that the reduced data matrix $\bar{T}$, being a representation of the full dataset, can be used as independent input data for other statistical modelling procedures, including artificial neural network methods. A key issue being the selection of the appropriate number of principal components.

Figure 6:
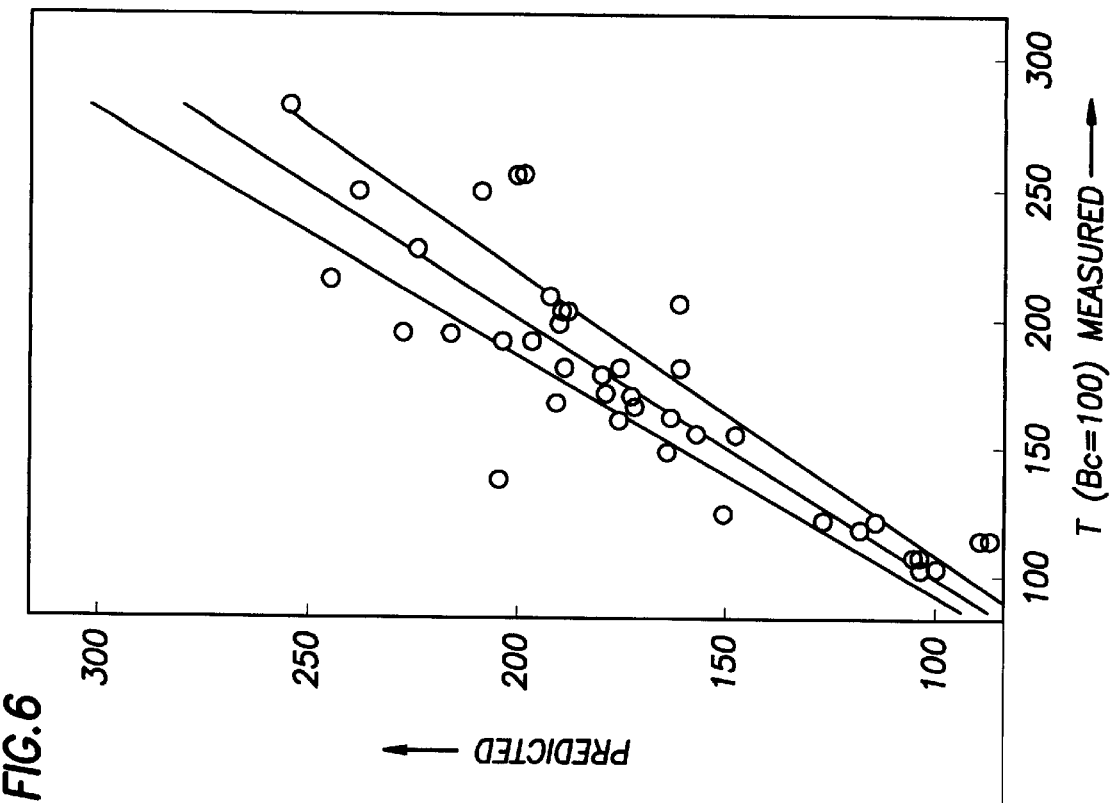
FIG. 6 shows the corresponding plot to FIG. 5 on the full input dataset defined below.
Figure 5:
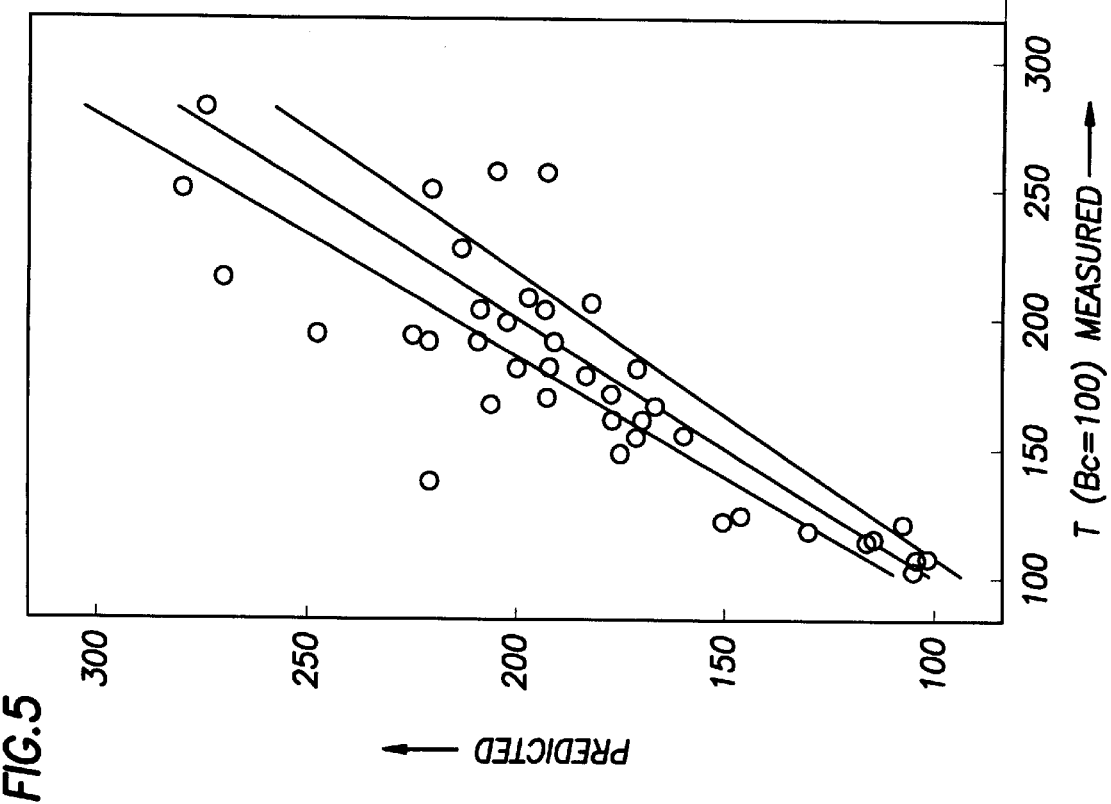
FIG. 5 shows the predicted thickening time plotted against measured thickening time predicted using FTIR spectra as the only input data.

FIG. 5 shows the cement thickening times, for a number of selected test cements, predicted using a previously calibrated neural network. Input data for the model are the FTIR spectra only reduced to 30 principal components. This number being determined as that which resulted in the lowest error in the prediction of thickening times for cements in an independent validation dataset. The corresponding results using the full dataset are shown in FIG. 6. In both cases the measured thickening time is plotted against that predicted by the model as a test of the accuracy.

TABLE 1

Error versus Number of Nodes

| NODES | % ER TRN | % ER VALID | N < 20% | N < 10% | N < 5% |
|---|---|---|---|---|---|
| 1 | 14.0 | 23 | 30 | 21 | 10 |
| 2 | 8.9 | 19.6 | 31 | 27 | 16 |
| 3 | 9.8 | 16.7 | 33 | 24 | 15 |
| 4 | 6.0 | 16.6 | 33 | 24 | 18 |
| 5 | 10.7 | 16.5 | 33 | 23 | 17 |
| 6 | 3.2 | 15.4 | 32 | 27 | 20 |
| 7 | 9.42 | 14.1 | 33 | 24 | 16 |
| 8 | 9.43 | 14.9 | 34 | 24 | 17 |
| 10 | 2.4 | 16.7 | 33 | 30 | 20 |
| 12 | 4.5 | 23.3 | 32 | 26 | 19 |

TABLE 2

Training Dataset

| No | $C_3S$ | $C_2S$ | $C_3A$ | Fer | $SO_3$ | MgO | LOI | IR | Alk | F. Lime | Blaine | NaCl | $CaCl_2$ | W/S | Depth | BHT | BHP | T/100 |
|---|---|---|---|---|---|---|---|---|---|---|---|---|---|---|---|---|---|---|
| 1G | 64 | 14 | 2.0 | 15.0 | 2.0 | 2.0 | 0.9 | 0.2 | 0.4 | 0.5 | 3100 | 0.0 | 0.0 | 44 | 2000 | 33 | 1540 | 216 |
| 2G | 64 | 14 | 2.0 | 15.0 | 2.0 | 2.0 | 0.9 | 0.2 | 0.4 | 0.5 | 3100 | 0.0 | 0.0 | 44 | 4000 | 39 | 2580 | 164 |
| 3G | 64 | 14 | 2.0 | 15.0 | 2.0 | 2.0 | 0.9 | 0.2 | 0.4 | 0.5 | 3100 | 0.0 | 0.0 | 44 | 6000 | 45 | 3870 | 145 |
| 4G | 64 | 14 | 2.0 | 15.0 | 2.0 | 2.0 | 0.9 | 0.2 | 0.4 | 0.5 | 3100 | 0.0 | 0.0 | 44 | 8000 | 52 | 5160 | 109 |
| 5G | 64 | 14 | 2.0 | 15.0 | 2.0 | 2.0 | 0.9 | 0.2 | 0.4 | 0.5 | 3100 | 6.0 | 0.0 | 60 | 2000 | 33 | 1540 | 497 |
| 6G | 64 | 14 | 2.0 | 15.0 | 2.0 | 2.0 | 0.9 | 0.2 | 0.4 | 0.5 | 3100 | 6.0 | 0.0 | 60 | 4000 | 39 | 2580 | 373 |
| 7G | 64 | 14 | 2.0 | 15.0 | 2.0 | 2.0 | 0.9 | 0.2 | 0.4 | 0.5 | 3100 | 6.0 | 0.0 | 60 | 6000 | 45 | 3870 | 292 |
| 8G | 64 | 14 | 2.0 | 15.0 | 2.0 | 2.0 | 0.9 | 0.2 | 0.4 | 0.5 | 3100 | 6.0 | 0.0 | 60 | 8000 | 52 | 5160 | 198 |
| 9G | 60.5 | 16 | 2.0 | 16.0 | 2.8 | 0.7 | 1.2 | 0.2 | 0.40 | 0.3 | 3700 | 0.0 | 0.0 | 44 | 8000 | 52 | 5160 | 111 |
| 1H | 62.7 | 15 | 1.3 | 16.0 | 2.7 | 0.7 | 1.2 | 0.1 | 0.29 | 0.25 | 2960 | 0.0 | 0.0 | 38 | 8000 | 52 | 5160 | 115 |
| 11H | 62.7 | 15 | 1.3 | 16.0 | 2.7 | 0.7 | 1.2 | 0.1 | 0.29 | 0.25 | 2960 | 0.0 | 0.0 | 46 | 8000 | 52 | 5160 | 175 |
| 12H | 58.9 | 16 | 1.5 | 16.0 | 2.8 | 0.7 | 1.2 | 0.23 | 0.29 | 0.40 | 2837 | 0.0 | 0.0 | 38 | 8000 | 52 | 5160 | 110 |
| 13H | 58.9 | 16 | 1.5 | 16.0 | 2.8 | 0.7 | 1.2 | 0.23 | 0.29 | 0.40 | 2837 | 0.0 | 0.0 | 46 | 8000 | 52 | 5160 | 160 |
| 14H | 58.9 | 16 | 1.5 | 16.0 | 2.8 | 0.7 | 1.2 | 0.23 | 0.29 | 0.40 | 2837 | 0.0 | 0.0 | 38 | 8000 | 52 | 5160 | 110 |
| 15H | 58.9 | 16 | 1.5 | 16.0 | 2.8 | 0.7 | 1.2 | 0.23 | 0.29 | 0.40 | 2837 | 0.0 | 0.0 | 46 | 8000 | 52 | 5160 | 160 |
| 16H | 56.0 | 17 | 1.8 | 16.0 | 2.7 | 0.7 | 1.2 | 0.26 | 0.29 | 0.35 | 2990 | 0.0 | 0.0 | 38 | 8000 | 52 | 5160 | 105 |
| 17H | 56.0 | 17 | 1.8 | 16.0 | 2.7 | 0.7 | 1.2 | 0.26 | 0.29 | 0.35 | 2990 | 0.0 | 0.0 | 46 | 8000 | 52 | 5160 | 149 |
| 18G | 54.0 | 22.0 | 1.7 | 15.0 | 2.3 | 0.8 | 0.8 | 0.15 | 0.40 | 0.35 | 3200 | 0.0 | 0.0 | 44 | 8000 | 52 | 5160 | 107 |
| 19G | 54.0 | 23.0 | 1.7 | 15.0 | 2.3 | 0.8 | 0.9 | 0.2 | 0.40 | 0.35 | 3200 | 0.0 | 0.0 | 44 | 8000 | 52 | 5160 | 117 |
| 20G | 54.0 | 23.0 | 1.7 | 15.0 | 2.4 | 0.8 | 1.0 | 0.2 | 0.37 | 0.35 | 3200 | 0.0 | 0.0 | 44 | 8000 | 52 | 5160 | 113 |
| 21G | 54.0 | 21.0 | 1.7 | 15.0 | 2.4 | 0.8 | 1.1 | 0.2 | 0.37 | 0.35 | 3200 | 0.0 | 0.0 | 44 | 8000 | 52 | 5160 | 110 |
| 22G | 55.7 | 20.7 | 1.71 | 15.6 | 2.37 | 0.84 | 0.97 | 0.15 | 0.38 | 0.35 | 3200 | 0.0 | 0.0 | 44 | 8000 | 52 | 5160 | 108 |
| 23G | 57.9 | 17.6 | 1.66 | 15.6 | 2.35 | 0.82 | 0.97 | 0.17 | 0.35 | 0.35 | 3200 | 0.0 | 0.0 | 44 | 8000 | 52 | 5160 | 114 |
| 24G | 59.3 | 16.9 | 1.60 | 15.1 | 2.26 | 0.81 | 1.06 | 0.17 | 0.33 | 0.35 | 3200 | 0.0 | 0.0 | 44 | 8000 | 52 | 5160 | 112 |
| 25G | 58.2 | 17.7 | 1.54 | 15.3 | 2.35 | 0.81 | 1.36 | 0.18 | 0.32 | 0.35 | 3200 | 0.0 | 0.0 | 44 | 8000 | 52 | 5160 | 114 |
| 26G | 57.9 | 18.0 | 1.34 | 15.21 | 2.30 | 0.79 | 1.04 | 0.16 | 0.35 | 0.35 | 3200 | 0.0 | 0.0 | 44 | 8000 | 52 | 5160 | 113 |
| 266 | 55.76 | 21.6 | 1.60 | 15.63 | 2.38 | 0.82 | 1.01 | 0.15 | 0.34 | 0.35 | 3200 | 0.0 | 0.0 | 44 | 8000 | 52 | 5160 | 116 |
| 28G | 56.40 | 19.7 | 1.61 | 15.5 | 2.29 | 0.84 | 1.09 | 0.14 | 0.34 | 0.35 | 3200 | 0.0 | 0.0 | 44 | 8000 | 52 | 5160 | 114 |
| 29G | 55.80 | 21.1 | 1.57 | 15.70 | 2.23 | 0.82 | 0.89 | 0.13 | 0.36 | 0.35 | 3200 | 0.0 | 0.0 | 44 | 8000 | 52 | 5160 | 112 |
| 30G | 57.60 | 19.3 | 1.63 | 15.53 | 2.19 | 0.82 | 1.94 | 0.15 | 0.36 | 0.35 | 3200 | 0.0 | 0.0 | 44 | 8000 | 52 | 5160 | 108 |
| 31G | 52.00 | 23.9 | 1.78 | 15.24 | 2.28 | 0.80 | 1.18 | 0.14 | 0.37 | 0.35 | 3200 | 0.0 | 0.0 | 44 | 8000 | 52 | 5160 | 111 |
| 32G | 54.00 | 22.39 | 1.69 | 15.31 | 2.26 | 0.77 | 1.01 | 0.16 | 0.35 | 0.35 | 3200 | 0.0 | 0.0 | 44 | 8000 | 52 | 5160 | 116 |
| 33G | 54.00 | 22.80 | 1.66 | 15.60 | 2.25 | 0.75 | 1.27 | 0.16 | 0.35 | 0.35 | 3200 | 0.0 | 0.0 | 44 | 8000 | 52 | 5160 | 116 |
| 34G | 57.30 | 19.30 | 1.32 | 15.00 | 2.41 | 0.75 | 1.12 | 0.17 | 0.34 | 0.35 | 3200 | 0.0 | 0.0 | 44 | 8000 | 52 | 5160 | 116 |
| 35G | 56.3 | 19.9 | 1.48 | 15.50 | 2.33 | 0.84 | 0.96 | 0.16 | 0.36 | 0.35 | 3200 | 0.0 | 0.0 | 44 | 8000 | 52 | 5160 | 114 |
| 36G | 54.5 | 21.4 | 1.50 | 15.51 | 2.31 | 0.75 | 1.27 | 0.16 | 0.34 | 0.35 | 3200 | 0.0 | 0.0 | 44 | 8000 | 52 | 5160 | 114 |
| 37G | 57.6 | 18.2 | 1.28 | 15.40 | 2.47 | 0.74 | 0.98 | 0.15 | 0.36 | 0.35 | 3200 | 0.0 | 0.0 | 44 | 8000 | 52 | 5160 | 115 |
| 38G | 58.2 | 17.9 | 1.47 | 15.30 | 2.24 | 0.82 | 0.89 | 0.16 | 0.36 | 0.35 | 3200 | 0.0 | 0.0 | 44 | 8000 | 52 | 5160 | 115 |
| 39G | 57.2 | 19.2 | 1.45 | 15.70 | 2.34 | 0.82 | 1.08 | 0.14 | 0.36 | 0.35 | 3200 | 0.0 | 0.0 | 44 | 8000 | 52 | 5160 | 113 |
| 40G | 58.1 | 19.3 | 1.63 | 14.80 | 2.44 | 0.83 | 0.99 | 0.16 | 0.34 | 0.35 | 3200 | 0.0 | 0.0 | 44 | 8000 | 52 | 5160 | 114 |
| 41G | 59.5 | 17.9 | 1.58 | 14.80 | 2.31 | 0.81 | 1.03 | 0.16 | 0.31 | 0.35 | 3200 | 0.0 | 0.0 | 44 | 8000 | 52 | 5160 | 115 |
| 42G | 57.5 | 19.1 | 1.94 | 14.60 | 2.18 | 0.77 | 1.04 | 0.18 | 0.32 | 0.35 | 3200 | 0.0 | 0.0 | 44 | 8000 | 52 | 5160 | 115 |
| 43G | 58.1 | 18.3 | 1.71 | 14.60 | 2.23 | 0.80 | 0.93 | 0.18 | 0.36 | 0.35 | 3200 | 0.0 | 0.0 | 44 | 8000 | 52 | 5160 | 113 |
| 44G | 54.7 | 22.1 | 1.72 | 14.80 | 2.29 | 0.76 | 1.07 | 0.19 | 0.32 | 0.35 | 3200 | 0.0 | 0.0 | 44 | 8000 | 52 | 5160 | 114 |
| 45G | 57.3 | 19.6 | 1.64 | 14.70 | 2.27 | 0.73 | 1.06 | 0.18 | 0.34 | 0.35 | 3200 | 0.0 | 0.0 | 44 | 8000 | 52 | 5160 | 116 |
| 46G | 56.7 | 20.4 | 1.77 | 18.20 | 2.26 | 0.77 | 1.00 | 0.17 | 0.3i | 0.35 | 3200 | 0.0 | 0.0 | 44 | 8000 | 52 | 5160 | 114 |
| 47G | 57.5 | 19.7 | 1.73 | 14.90 | 2.07 | 0.77 | 1.20 | 0.19 | 0.31 | 0.35 | 3200 | 0.0 | 0.0 | 44 | 8000 | 52 | 5160 | 113 |
| 48G | 58.0 | 19.2 | 1.78 | 14.90 | 2.28 | 0.74 | 1.13 | 0.16 | 0.34 | 0.35 | 3200 | 0.0 | 0.0 | 44 | 8000 | 52 | 5160 | 115 |
| 49G | 57.6 | 28.9 | 1.49 | 14.90 | 2.20 | 0.72 | 1.07 | 0.18 | 0.34 | 0.35 | 3200 | 0.0 | 0.0 | 44 | 8000 | 52 | 5160 | 107 |
| 50G | 57.1 | 19.8 | 1.38 | 15.05 | 2.21 | 0.75 | 1.00 | 0.17 | 0.34 | 0.35 | 3200 | 0.0 | 0.0 | 44 | 8000 | 52 | 5160 | 113 |
| 51G | 54.0 | 20 | 2.50 | 14.5 | 1.70 | 0.60 | 1.2 | 0.20 | 0.45 | 0.4 | 3110 | 0.0 | 0.0 | 44 | 8000 | 52 | 5160 | 91 |
| 52G | 55.0 | 20 | 2.5 | 14.5 | 1.70 | 0.60 | 0.8 | 0.20 | 0.54 | 0.4 | 3110 | 0.0 | 0.0 | 44 | 8000 | 52 | 5160 | 104 |
| 53G | 55.0 | 20 | 2.0 | 14.50 | 1.80 | 0.60 | 0.9 | 0.20 | 0.44 | 0.4 | 3090 | 0.0 | 0.0 | 44 | 8000 | 52 | 5160 | 100 |
| 54G | 53.0 | 20 | 2.0 | 14.5 | 1.80 | 0.70 | 0.9 | 0.20 | 0.53 | 0.4 | 3090 | 0.0 | 0.0 | 44 | 8000 | 52 | 5160 | 95 |
| 55G | 52.0 | 20 | 2.3 | 14.6 | 1.80 | 0.60 | 0.9 | 0.20 | 0.55 | 0.4 | 3120 | 0.0 | 0.0 | 44 | 8000 | 52 | 5160 | 95 |
| 56G | 55.0 | 20 | 2.2 | 14.6 | 1.70 | 0.60 | 1.1 | 0.20 | 0.41 | 0.4 | 3140 | 0.0 | 0.0 | 44 | 8000 | 52 | 5160 | 100 |
| 57G | 52.0 | 20 | 2.4 | 14.7 | 1.90 | 0.60 | 1.0 | 0.20 | 0.54 | 0.4 | 3170 | 0.0 | 0.0 | 44 | 8000 | 52 | 5160 | 93 |
| 58G | 54.0 | 20 | 1.9 | 15.2 | 1.70 | 0.70 | 1.1 | 0.20 | 0.35 | 0.4 | 3010 | 0.0 | 0.0 | 44 | 8000 | 52 | 5160 | 105 |
| 59G | 58.0 | 20 | 2.3 | 13.4 | 1.80 | 0.60 | 1.1 | 0.20 | 0.33 | 0.4 | 3110 | 0.0 | 0.0 | 44 | 8000 | 52 | 5160 | 106 |
| 60G | 54.0 | 20 | 2.4 | 13.8 | 1.90 | 0.60 | 1.0 | 0.20 | 0.51 | 0.4 | 3260 | 0.0 | 0.0 | 44 | 8000 | 52 | 5160 | 105 |
| 61G | 53.0 | 20 | 2.5 | 14.0 | 1.80 | 0.60 | 1.1 | 0.20 | 0.50 | 0.4 | 3070 | 0.0 | 0.0 | 44 | 8000 | 52 | 5160 | 102 |
| 62G | 54.0 | 20 | 2.5 | 14.0 | 1.90 | 0.60 | 1.1 | 0.20 | 0.54 | 0.4 | 3010 | 0.0 | 0.0 | 44 | 8000 | 52 | 5160 | 96 |
| 63G | 52.0 | 20 | 2.3 | 14.9 | 1.90 | 0.70 | 1.2 | 0.20 | 0.55 | 0.4 | 3020 | 0.0 | 0.0 | 44 | 8000 | 52 | 5160 | 100 |
| 64G | 53.0 | 20 | 2.3 | 15.4 | 1.90 | 0.70 | 1.2 | 0.20 | 0.57 | 0.4 | 3250 | 0.0 | 0.0 | 44 | 8000 | 52 | 5160 | 96 |
| 66A | 60 | 10 | 11 | 7 | 2.5 | 2.0 | 0.9 | 0.20 | 0.4 | 0.4 | 3250 | 0.0 | 0.0 | 46 | 1000 | 27 | 1020 | 324 |
| 67A | 60 | 10 | 11 | 7 | 2.5 | 2.0 | 0.9 | 0.20 | 0.4 | 0.4 | 3250 | 0.0 | 0.0 | 46 | 2000 | 33 | 1540 | 264 |
| 68A | 60 | 10 | 11 | 7 | 2.5 | 2.0 | 0.9 | 0.20 | 0.4 | 0.4 | 3250 | 0.0 | 0.0 | 46 | 4000 | 39 | 2580 | 202 |
| 69A | 60 | 10 | 11 | 7 | 2.5 | 2.0 | 0.9 | 0.20 | 0.4 | 0.4 | 3250 | 0.0 | 0.0 | 46 | 6000 | 45 | 3870 | 128 |
| 70A | 60 | 10 | 11 | 7 | 2.5 | 2.0 | 0.9 | 0.20 | 0.4 | 0.4 | 3250 | 6.0 | 0.0 | 63 | 1000 | 27 | 1020 | 1149 |
| 71A | 60 | 10 | 11 | 7 | 2.5 | 2.0 | 0.9 | 0.20 | 0.4 | 0.4 | 3250 | 6.0 | 0.0 | 63 | 2000 | 33 | 1540 | 654 |
| 72A | 60 | 10 | 11 | 7 | 2.5 | 2.0 | 0.9 | 0.20 | 0.4 | 0.4 | 3250 | 6.0 | 0.0 | 63 | 4000 | 39 | 2580 | 345 |
| 73A | 60 | 10 | 11 | 7 | 2.5 | 2.0 | 0.9 | 0.20 | 0.4 | 0.4 | 3250 | 6.0 | 0.0 | 63 | 6000 | 45 | 3870 | 309 |
| 74B | 61 | 17 | 15 | 2 | 2.5 | 2.0 | 0.9 | 0.20 | 0.4 | 0.4 | 3200 | 0.0 | 0.0 | 46 | 1000 | 27 | 1020 | 431 |
| 75B | 61 | 17 | 15 | 2 | 2.5 | 2.0 | 0.9 | 0.20 | 0.4 | 0.4 | 3200 | 0.0 | 0.0 | 46 | 2000 | 33 | 1540 | 342 |
| 75B | 61 | 17 | 15 | 2 | 2.5 | 2.0 | 0.9 | 0.20 | 0.4 | 0.4 | 3200 | 0.0 | 0.0 | 46 | 4000 | 39 | 2580 | 235 |

TABLE 2-continued

Training Dataset

| No | $C_3S$ | $C_2S$ | $C_3A$ | Fer | $SO_3$ | MgO | LOI | IR | Alk | F. Lime | Blaine | NaCl | $CaCl_2$ | W/S | Depth | BHT | BHP | T/100 |
|---|---|---|---|---|---|---|---|---|---|---|---|---|---|---|---|---|---|---|
| 76B | 61 | 17 | 15 | 2 | 2.5 | 2.0 | 0.9 | 0.20 | 0.4 | 0.4 | 3200 | 0.0 | 0.0 | 46 | 6000 | 45 | 3870 | 132 |
| 77B | 61 | 17 | 15 | 2 | 2.5 | 2.0 | 0.9 | 0.20 | 0.4 | 0.4 | 3200 | 0.0 | 0.0 | 46 | 8000 | 52 | 5160 | 105 |
| 78B | 61 | 17 | 15 | 2 | 2.5 | 2.0 | 0.9 | 0.20 | 0.4 | 0.4 | 3200 | 0.0 | 0.0 | 46 | 10000 | 62 | 7480 | 91 |
| 79B | 61 | 17 | 15 | 2 | 2.5 | 2.0 | 0.9 | 0.20 | 0.4 | 0.4 | 3200 | 6.0 | 0.0 | 63 | 1000 | 27 | 1020 | 1236 |
| 80B | 61 | 17 | 15 | 2 | 2.5 | 2.0 | 0.9 | 0.20 | 0.4 | 0.4 | 3200 | 6.0 | 0.0 | 63 | 2000 | 33 | 1540 | 678 |
| 81B | 61 | 17 | 15 | 2 | 2.5 | 2.0 | 0.9 | 0.20 | 0.4 | 0.4 | 3200 | 6.0 | 0.0 | 63 | 4000 | 39 | 2580 | 360 |
| 82B | 61 | 17 | 15 | 2 | 2.5 | 2.0 | 0.9 | 0.20 | 0.4 | 0.4 | 3200 | 6.0 | 0.0 | 63 | 6000 | 45 | 3870 | 336 |
| 83B | 61 | 17 | 15 | 2 | 2.5 | 2.0 | 0.9 | 0.20 | 0.4 | 0.4 | 3200 | 6.0 | 0.0 | 63 | 8000 | 52 | 5160 | 276 |
| 84B | 61 | 17 | 15 | 2 | 2.5 | 2.0 | 0.9 | 0.20 | 0.4 | 0.4 | 3200 | 6.0 | 0.0 | 63 | 10000 | 62 | 7480 | 219 |
| 85C | 58 | 16 | 10 | 10 | 3.0 | 2.0 | 1.2 | 0.20 | 0.4 | 0.4 | 4400 | 0.0 | 0.0 | 56 | 1000 | 27 | 1020 | 330 |
| 86C | 58 | 16 | 10 | 10 | 3.0 | 2.0 | 1.2 | 0.20 | 0.4 | 0.4 | 4400 | 0.0 | 0.0 | 56 | 2000 | 33 | 1540 | 309 |
| 87C | 58 | 16 | 10 | 10 | 3.0 | 2.0 | 1.2 | 0.20 | 0.4 | 0.4 | 4400 | 0.0 | 0.0 | 56 | 4000 | 39 | 2580 | 220 |
| 88C | 58 | 16 | 10 | 10 | 3.0 | 2.0 | 1.2 | 0.20 | 0.4 | 0.4 | 4400 | 0.0 | 0.0 | 56 | 6000 | 45 | 3870 | 155 |
| 89C | 58 | 16 | 10 | 10 | 3.0 | 2.0 | 1.2 | 0.20 | 0.4 | 0.4 | 4400 | 6.0 | 0.0 | 77 | 1000 | 27 | 1020 | 820 |
| 90C | 58 | 16 | 10 | 10 | 3.0 | 2.0 | 1.2 | 0.20 | 0.4 | 0.4 | 4400 | 6.0 | 0.0 | 77 | 2000 | 33 | 1540 | 735 |
| 91C | 58 | 16 | 10 | 10 | 3.0 | 2.0 | 1.2 | 0.20 | 0.4 | 0.4 | 4400 | 6.0 | 0.0 | 77 | 4000 | 39 | 2580 | 500 |
| 92C | 58 | 16 | 10 | 10 | 3.0 | 2.0 | 1.2 | 0.20 | 0.4 | 0.4 | 4400 | 6.0 | 0.0 | 77 | 6000 | 45 | 3870 | 305 |
| 93A | 62 | 10 | 11 | 7 | 2.2 | 1.3 | 2.0 | 0.5 | 0.4 | 0.4 | 3250 | 0.0 | 0.0 | 46 | 1000 | 27 | 1020 | 430 |
| 94A | 62 | 10 | 11 | 7 | 2.2 | 1.3 | 2.0 | 0.5 | 0.4 | 0.4 | 3250 | 0.0 | 0.0 | 46 | 6000 | 45 | 3870 | 145 |
| 95B | 61 | 17 | 1 | 16 | 2.0 | 0.7 | 1.2 | 0.3 | 0.4 | 0.4 | 3200 | 0.0 | 0.0 | 46 | 1000 | 27 | 1020 | 400 |
| 96B | 61 | 17 | 1 | 16 | 2.2 | 0.7 | 1.2 | 0.3 | 0.4 | 0.4 | 3200 | 0.0 | 0.0 | 46 | 6000 | 45 | 3870 | 165 |
| 97H | 57 | 19 | 1.2 | 14.0 | 2.4 | 0.7 | 1.0 | 0.3 | 0.4 | 0.4 | 2330 | 0.0 | 0.0 | 38 | 8000 | 52 | 5160 | 123 |
| 98H | 54 | 23 | 1.3 | 14.3 | 2.1 | 0.7 | 1.0 | 0.3 | 0.4 | 0.4 | 1900 | 0.0 | 0.0 | 38 | 8000 | 52 | 5160 | 156 |
| 99H | 57 | 21 | 2.3 | 14.3 | 1.8 | 0.7 | 1.0 | 0.3 | 0.4 | 0.4 | 2420 | 0.0 | 0.0 | 38 | 8000 | 52 | 5160 | 138 |
| 100H | 56 | 22 | 1.5 | 14.0 | 2.3 | 0.7 | 1.0 | 0.3 | 0.4 | 0.4 | 2020 | 0.0 | 0.0 | 38 | 8000 | 52 | 5160 | 154 |
| 101H | 48 | 28 | 3.5 | 11.5 | 2.0 | 0.7 | 1.0 | 0.3 | 0.4 | 0.4 | 2220 | 0.0 | 0.0 | 38 | 8000 | 52 | 5160 | 138 |
| 102H | 50 | 27 | 2.7 | 11.8 | 2.1 | 0.7 | 1.0 | 0.3 | 0.4 | 0.4 | 2270 | 0.0 | 0.0 | 38 | 8000 | 52 | 5160 | 133 |
| 103H | 46 | 29 | 0.8 | 16.6 | 2.8 | 0.7 | 1.0 | 0.3 | 0.4 | 0.4 | 2740 | 0.0 | 0.0 | 38 | 8000 | 52 | 5160 | 106 |
| 104H | 49 | 25 | 0.3 | 17.0 | 2.8 | 0.7 | 1.0 | 0.3 | 0.4 | 0.4 | 2810 | 0.0 | 0.0 | 38 | 8000 | 52 | 5160 | 117 |
| 105H | 62 | 14 | 3.1 | 10.6 | 2.4 | 0.7 | 1.0 | 0.3 | 0.4 | 0.4 | 3360 | 0.0 | 0.0 | 38 | 8000 | 52 | 5160 | 46 |
| 106A | 57 | 17 | 7.7 | 8.5 | 2.8 | 0.7 | 1.0 | 0.3 | 0.4 | 0.4 | 3680 | 0.0 | 0.0 | 38 | 8000 | 52 | 5160 | 30 |
| 107A | 56 | 18 | 4.6 | 9.8 | 2.6 | 0.7 | 1.0 | 0.3 | 0.4 | 0.4 | 2650 | 0.0 | 0.0 | 33 | 8000 | 52 | 5160 | 101 |
| 108G | 67 | 10 | 1.0 | 16 | 1.8 | 1.15 | 0.88 | 0.04 | 0.62 | 0.4 | 2860 | 0.0 | 0.0 | 45 | 8000 | 52 | 5160 | 111 |
| 109G | 60 | 16 | 1 | 13 | 2.2 | 0.7 | 1.0 | 0.3 | 0.4 | 0.4 | 3190 | 0.0 | 0.0 | 45 | 8000 | 52 | 5160 | 99 |
| 110G | 64 | 12 | 0.4 | 12.9 | 2.5 | 0.7 | 1.6 | 0.01 | 0.06 | 2.9 | 3910 | 0.0 | 0.0 | 45 | 8000 | 52 | 5160 | 132 |
| 111G | 53 | 13.7 | 10.4 | 9.1 | 2.5 | 0.7 | 1.1 | 1.9 | 0.29 | 0.5 | 3910 | 0.0 | 0.0 | 46 | 6000 | 45 | 3870 | 130 |
| 112G | 56.5 | 21.1 | 5.2 | 10.3 | 2.2 | 1.33 | 1.0 | 1.0 | 0.5 | 0.0 | 2753 | 0.0 | 0.0 | 44 | 8000 | 52 | 5160 | 106 |
| 113G | 57.0 | 20 | 2.4 | 15.0 | 1.9 | 0.55 | 1.0 | 0.2 | 0.5 | 0.0 | 2753 | 0.0 | 0.0 | 44 | 8000 | 52 | 5160 | 104 |
| 114G | 55.6 | 20 | 3.24 | 14.3 | 2.54 | 1.36 | 1.5 | 0.2 | 0.57 | 0.0 | 2800 | 0.0 | 0.0 | 44 | 8000 | 52 | 5160 | 92 |
| 115G | 60 | 17 | 1 | 16 | 2.0 | 0.6 | 1.2 | 0.3 | 0.4 | 0.4 | 3300 | 0.0 | 0.0 | 46 | 8000 | 52 | 5160 | 115 |
| 116G | 60 | 17 | 1 | 16 | 2.0 | 0.6 | 1.2 | 0.3 | 0.4 | 0.4 | 3300 | 0.45 | 0.011 | 46 | 8000 | 52 | 5160 | 65 |
| 117G | 60 | 17 | 1 | 16 | 2.0 | 0.6 | 1.2 | 0.3 | 0.4 | 0.4 | 3300 | 0.00 | 0.39 | 46 | 8000 | 52 | 5160 | 50 |
| 118A | 62 | 10 | 11 | 7 | 2.2 | 1.3 | 2.0 | 0.5 | 0.4 | 0.4 | 3250 | 0.45 | 0.01 | 46 | 1000 | 27 | 1020 | 375 |
| 119A | 62 | 10 | 11 | 7 | 2.2 | 1.3 | 2.0 | 0.5 | 0.4 | 0.4 | 3250 | 0.45 | 0.01 | 46 | 6000 | 45 | 3870 | 100 |
| 120A | 62 | 10 | 11 | 7 | 2.2 | 1.3 | 2.0 | 0.5 | 0.4 | 0.4 | 3250 | 0.0 | 0.39 | 46 | 1000 | 27 | 1020 | 215 |
| 121A | 62 | 10 | 11 | 7 | 2.2 | 1.3 | 2.0 | 0.5 | 0.4 | 0.4 | 3250 | 0.0 | 0.39 | 46 | 6000 | 45 | 3870 | 85 |
| 122B | 61 | 17 | 1 | 16 | 2.0 | 0.7 | 1.2 | 0.3 | 0.4 | 0.4 | 3200 | 0.45 | 0.01 | 46 | 1000 | 27 | 1020 | 365 |
| 123B | 61 | 17 | 1 | 16 | 2.2 | 0.7 | 1.2 | 0.3 | 0.4 | 0.4 | 3200 | 0.45 | 0.01 | 46 | 6000 | 45 | 3870 | 95 |
| 124B | 61 | 17 | 1 | 16 | 2.0 | 0.7 | 1.2 | 0.3 | 0.4 | 0.4 | 3200 | 0.0 | 0.39 | 46 | 1000 | 27 | 1020 | 190 |
| 125B | 61 | 17 | 1 | 16 | 2.2 | 0.7 | 1.2 | 0.3 | 0.4 | 0.4 | 3200 | 0.0 | 0.39 | 46 | 6000 | 45 | 3870 | 65 |
| 126A | 60 | 10 | 1 | 7 | 2.5 | 2.0 | 0.9 | 0.20 | 0.4 | 0.4 | 3250 | 0.45 | 0.01 | 47 | 1000 | 27 | 1020 | 268 |
| 127A | 60 | 10 | 1 | 7 | 2.5 | 2.0 | 0.9 | 0.20 | 0.4 | 0.4 | 3250 | 0.45 | 0.01 | 47 | 2000 | 33 | 1540 | 220 |
| 128A | 60 | 10 | 11 | 7 | 2.5 | 2.0 | 0.9 | 0.20 | 0.4 | 0.4 | 3250 | 0.45 | 0.01 | 47 | 4000 | 39 | 2580 | 134 |
| 129A | 60 | 10 | 11 | 7 | 2.5 | 2.0 | 0.9 | 0.20 | 0.4 | 0.4 | 3250 | 0.45 | 0.01 | 47 | 6000 | 45 | 3870 | 117 |
| 130B | 61 | 17 | 15 | 2 | 2.5 | 2.0 | 0.9 | 0.20 | 0.4 | 0.4 | 3200 | 0.45 | 0.01 | 47 | 1000 | 27 | 1020 | 315 |
| 131B | 61 | 17 | 15 | 2 | 2.5 | 2.0 | 0.9 | 0.20 | 0.4 | 0.4 | 3200 | 0.45 | 0.01 | 47 | 2000 | 33 | 1540 | 222 |
| 132B | 61 | 17 | 15 | 2 | 2.5 | 2.0 | 0.9 | 0.20 | 0.4 | 0.4 | 3200 | 0.45 | 0.01 | 47 | 4000 | 39 | 2580 | 130 |
| 133B | 61 | 17 | 15 | 2 | 2.5 | 2.0 | 0.9 | 0.20 | 0.4 | 0.4 | 3200 | 0.45 | 0.01 | 47 | 6000 | 45 | 3870 | 116 |
| 134B | 61 | 17 | 15 | 2 | 2.5 | 2.0 | 0.9 | 0.20 | 0.4 | 0.4 | 3200 | 0.45 | 0.01 | 47 | 8000 | 52 | 5160 | 87 |
| 135B | 61 | 17 | 15 | 2 | 2.5 | 2.0 | 0.9 | 0.20 | 0.4 | 0.4 | 3200 | 0.45 | 0.01 | 47 | 10000 | 62 | 7480 | 74 |
| 136C | 58 | 16 | 10 | 10 | 3.0 | 2.0 | 1.2 | 0.20 | 0.4 | 0.4 | 4400 | 0.45 | 0.01 | 57 | 1000 | 27 | 1020 | 282 |
| 137C | 58 | 16 | 10 | 10 | 3.0 | 2.0 | 1.2 | 0.20 | 0.4 | 0.4 | 4400 | 0.45 | 0.01 | 57 | 2000 | 33 | 1540 | 230 |
| 138C | 58 | 16 | 10 | 10 | 3.0 | 2.0 | 1.2 | 0.20 | 0.4 | 0.4 | 4400 | 0.45 | 0.01 | 57 | 4000 | 39 | 2580 | 159 |
| 139C | 58 | 16 | 10 | 10 | 3.0 | 2.0 | 1.2 | 0.20 | 0.4 | 0.4 | 4400 | 0.45 | 0.01 | 57 | 6000 | 45 | 3870 | 121 |
| 140G | 64 | 14 | 2.0 | 15.0 | 2.0 | 2.0 | 0.9 | 0.2 | 0.4 | 0.5 | 3100 | 0.45 | 0.01 | 45 | 2000 | 33 | 1540 | 216 |
| 141G | 64 | 14 | 2.0 | 15.0 | 2.0 | 2.0 | 0.9 | 0.2 | 0.4 | 0.5 | 3100 | 0.45 | 0.01 | 45 | 4000 | 39 | 2580 | 164 |
| 142G | 64 | 14 | 2.0 | 15.0 | 2.0 | 2.0 | 0.9 | 0.2 | 0.4 | 0.5 | 3100 | 0.45 | 0.01 | 45 | 6000 | 45 | 3870 | 145 |
| 143G | 64 | 14 | 2.0 | 15.0 | 2.0 | 2.0 | 0.9 | 0.2 | 0.4 | 0.5 | 3100 | 0.45 | 0.01 | 45 | 8000 | 52 | 5160 | 109 |
| 144B | 61 | 17 | 15 | 2 | 2.5 | 2.0 | 0.9 | 0.20 | 0.4 | 0.4 | 3200 | 0.45 | 0.2 | 47 | 1000 | 27 | 1020 | 275 |
| 145B | 61 | 17 | 15 | 2 | 2.5 | 2.0 | 0.9 | 0.20 | 0.4 | 0.4 | 3200 | 0.45 | 0.2 | 47 | 2000 | 33 | 1540 | 178 |
| 146B | 61 | 17 | 15 | 2 | 2.5 | 2.0 | 0.9 | 0.20 | 0.4 | 0.4 | 3200 | 0.45 | 0.2 | 47 | 4000 | 39 | 2580 | 157 |
| 147B | 61 | 17 | 15 | 2 | 2.5 | 2.0 | 0.9 | 0.20 | 0.4 | 0.4 | 3200 | 0.45 | 0.4 | 47 | 1000 | 27 | 1020 | 215 |
| 148B | 61 | 17 | 15 | 2 | 2.5 | 2.0 | 0.9 | 0.20 | 0.4 | 0.4 | 3200 | 0.45 | 0.4 | 47 | 2000 | 33 | 1540 | 141 |
| 149B | 61 | 17 | 15 | 2 | 2.5 | 2.0 | 0.9 | 0.20 | 0.4 | 0.4 | 3200 | 0.45 | 0.4 | 47 | 4000 | 39 | 2580 | 111 |
| 150B | 61 | 17 | 15 | 2 | 2.5 | 2.0 | 0.9 | 0.20 | 0.4 | 0.4 | 3200 | 0.45 | 0.8 | 47 | 1000 | 27 | 1020 | 187 |

TABLE 2-continued

Training Dataset

| No | $C_3S$ | $C_2S$ | $C_3A$ | Fer | $SO_3$ | MgO | LOI | IR | Alk | F. Lime | Blaine | NaCl | $CaCl_2$ | W/S | Depth | BHT | BHP | T/100 |
|---|---|---|---|---|---|---|---|---|---|---|---|---|---|---|---|---|---|---|
| 151B | 61 | 17 | 15 | 2 | 2.5 | 2.0 | 0.9 | 0.20 | 0.4 | 0.4 | 3200 | 0.45 | 0.8 | 47 | 2000 | 33 | 1540 | 128 |
| 152B | 61 | 17 | 15 | 2 | 2.5 | 2.0 | 0.9 | 0.20 | 0.4 | 0.4 | 3200 | 0.45 | 0.8 | 47 | 4000 | 39 | 2580 | 109 |
| 153G | 64 | 14 | 2.0 | 15.0 | 2.0 | 2.0 | 0.9 | 0.2 | 0.4 | 0.5 | 3100 | 0.45 | 0.39 | 46 | 2000 | 35 | 1540 | 145 |
| 154G | 64 | 14 | 2.0 | 15.0 | 2.0 | 2.0 | 0.9 | 0.2 | 0.4 | 0.5 | 3100 | 0.00 | 0.39 | 44 | 4000 | 33 | 2580 | 95 |
| 155B | 61 | 17 | 15 | 2 | 2.5 | 2.0 | 0.9 | 0.20 | 0.4 | 0.4 | 3200 | 3.4 | 0.0 | 46 | 6000 | 45 | 3870 | 169 |
| 156B | 61 | 17 | 15 | 2 | 2.5 | 2.0 | 0.9 | 0.20 | 0.4 | 0.4 | 3200 | 3.4 | 0.0 | 46 | 8000 | 52 | 5160 | 136 |
| 157B | 61 | 17 | 15 | 2 | 2.5 | 2.0 | 0.9 | 0.20 | 0.4 | 0.4 | 3200 | 3.4 | 0.0 | 47 | 10000 | 62 | 7480 | 112 |
| 158G | 64 | 14 | 2.0 | 15.0 | 2.0 | 2.0 | 0.9 | 0.2 | 0.4 | 0.5 | 2600 | 0.00 | 0.00 | 38 | 2000 | 33 | 1540 | 216 |
| 159G | 64 | 14 | 2.0 | 15.0 | 2.0 | 2.0 | 0.9 | 0.2 | 0.4 | 0.5 | 2600 | 0.00 | 0.00 | 38 | 4000 | 39 | 2510 | 164 |
| 160G | 64 | 14 | 2.0 | 15.0 | 2.0 | 2.0 | 0.9 | 0.2 | 0.4 | 0.5 | 2600 | 0.00 | 0.00 | 38 | 6000 | 45 | 3870 | 145 |
| 161G | 64 | 14 | 2.0 | 15.0 | 2.0 | 2.0 | 0.9 | 0.2 | 0.4 | 0.5 | 2600 | 0.00 | 0.00 | 38 | 8000 | 52 | 5160 | 109 |
| 162G | 64 | 14 | 2.0 | 15.0 | 2.0 | 2.0 | 0.9 | 0.2 | 0.4 | 0.5 | 2600 | 0.45 | 0.01 | 39 | 2000 | 33 | 1540 | 162 |
| 163G | 64 | 14 | 2.0 | 15.0 | 2.0 | 2.0 | 0.9 | 0.2 | 0.4 | 0.5 | 2600 | 0.45 | 0.01 | 39 | 4000 | 39 | 2580 | 106 |
| 164G | 64 | 14 | 2.0 | 15.0 | 2.0 | 2.0 | 0.9 | 0.2 | 0.4 | 0.5 | 2600 | 0.45 | 0.01 | 39 | 6000 | 45 | 3870 | 89 |
| 165G | 64 | 14 | 2.0 | 15.0 | 2.0 | 2.0 | 0.9 | 0.2 | 0.4 | 0.5 | 2600 | 0.45 | 0.01 | 39 | 8000 | 52 | 5160 | 69 |
| 166G | 64 | 14 | 2.0 | 15.0 | 2.0 | 2.0 | 0.9 | 0.2 | 0.4 | 0.5 | 2600 | 6.00 | 0.00 | 52 | 2000 | 33 | 1540 | 466 |
| 167G | 64 | 14 | 2.0 | 15.0 | 2.0 | 2.0 | 0.9 | 0.2 | 0.4 | 0.5 | 2600 | 6.00 | 0.00 | 52 | 4000 | 39 | 2580 | 350 |
| 168G | 64 | 14 | 2.0 | 15.0 | 2.0 | 2.0 | 0.9 | 0.2 | 0.4 | 0.5 | 2600 | 6.00 | 0.00 | 52 | 6000 | 45 | 3870 | 260 |
| 169G | 64 | 14 | 2.0 | 15.0 | 2.0 | 2.0 | 0.9 | 0.2 | 0.4 | 0.5 | 2600 | 6.00 | 0.00 | 52 | 8000 | 52 | 5160 | 176 |

We claim:

1. A method of predicting a time developing property of a cement or a cement slurry comprising forming a calibration model by determining infrared spectra for a series of known cement compositions;

obtaining the infrared spectrum of said cement or cement slurry; and obtaining a prediction of said time-developing property by applying values representing said infrared spectrum of said cement or cement slurry to the model and correlating these with measured values of the time-developing property for the cement compositions in the series.

2. The method of claim 1 in which the Fourier transform infrared spectrum is obtained, and the cement is an oil well cement or oil well cement slurry.

3. The method of claim 2 in which the time-developing property is the thickening time.

4. A method of predicting a time developing property of a cement or a cement slurry comprising forming a spectrum model by determining spectra, including infrared spectra, for a series of known cement compositions;

obtaining the infrared spectrum of said cement or cement slurry; and obtaining a prediction of said time-developing property by applying values representing said infrared spectrum of said cement or cement slurry to the model and correlating these with measured values of the time-developing property for the cement compositions in the series.

5. The method of claim 4 in which the Fourier transform infrared spectrum is obtained, and the cement is an oil well cement or oil well cement slurry.

6. The method of claim 5 in which the time-developing property is the thickening time of the cement slurry.

7. A method of predicting a time developing property of an oil well cement or an oil well cement slurry comprising forming a calibration model by determining infrared spectra for a series of known cement compositions;

obtaining the Fourier transform infrared spectrum of said cement or cement slurry; and obtaining a prediction of said time-developing property by applying values representing said infrared spectrum of said cement or cement slurry to the model, including inputting values representing the infrared spectrum of said cement or cement slurry to a neural network device configured to output a value representative of the time-developing property, the neural network device being a) configured to utilize each of said values as input values, b) provided with at least one hidden layer of at least one node, and c) trained with a dataset comprising a series of values of said infrared spectrum and values corresponding to the time-developing property, and correlating these with measured values of the time-developing property for the cement compositions in the series.

8. The method of claim 7 wherein the neural network device is configured to have one or two hidden layers, each with 1 to 12 nodes.

9. The method of claim 8 in which the time-developing property is the thickening time.

10. The method of claim 7 in which the time-developing property is the thickening time.

11. A method of predicting a time developing property of an oil well cement or an oil well cement slurry comprising forming a spectrum model by determining spectra, including infrared spectra, for a series of known cement compositions;

obtaining the Fourier transform infrared spectrum of said cement or cement slurry; and obtaining a prediction of said time-developing property by applying values representing said infrared spectrum of said cement or cement slurry to the model, inputting values representing the infrared spectrum of said cement or cement slurry to a neural network device configured to output a value representative of the time-developing property, the neural network device being a) configured to utilize each of said values as input values, b) provided with at least one hidden layer of at least one node, and c) trained with a dataset comprising a series of values of said infrared spectrum and values corresponding to the time-developing property, and correlating these with measured values of the time-developing property for the cement compositions in the series.

12. The method of claim 11 wherein the neural network device is configured to have one or two hidden layers, each with 1 to 12 nodes.

13. The method of claim 12 in which the time-developing property is the thickening time.

14. The method of claim 11 wherein the spectrum model comprises data from at least nine properties selected from (a) percentage by weight of each of the minerals tricalcium silicate, dicalcium silicate, tricalcium aluminate and calcium alumino-ferrite;

(b) total percentage by weight of sulphate;

(c) Blaine surface area (d) Percentage by weight of each of MgO, total alkali content and free lime;

(a) percentage loss, by weight, on ignition;

(f) Insoluble residue (IR);

(g) Water-to-solid ratio for all cement slurries (W/S);

(h) Weight percent of sodium chloride (NaCl) retarder in some cement blends;

(i) Weight percent of calcium chloride ($CaCl_2$) accelerator in some cement blends;

(j) Thickening time schedules defined by well depth (Depth), bottom hole temperature (BHT) and bottom hole pressure (BHP) (3 input variables);

(k) Thickening time to 100 Bearden units (T/100); and (l) Particle size distribution;

(m) Percentage by weight of calcium hydroxide and calcium carbonate.

15. The method of claim 14 in which the time-developing property is the thickening time.

16. The method of claim 11 in which the time-developing property is the thickening time.

* * * * *